US012629365B2

(12) United States Patent
Nirogi et al.

(10) Patent No.: US 12,629,365 B2

(45) Date of Patent: May 19, 2026

(54) PHARMACEUTICAL COMPOSITIONS OF 5-HT$_6$ RECEPTOR ANTAGONIST

(71) Applicant: SUVEN LIFE SCIENCES LIMITED, Banjara Hills (IN)

(72) Inventors: Ramakrishna Nirogi, Hyderabad (IN); Koteshwara Mudigonda, Hyderabad (IN); Dhanunjay Kumar Dogiparti, Hyderabad (IN); Venkateswarlu Jasti, Hyderabad (IN)

(73) Assignee: SUVEN LIFE SCIENCES LIMITED, Banjara Hills (IN)

( * ) Notice: Subject to any disclaimer, the term of this patent is extended or adjusted under 35 U.S.C. 154(b) by 0 days.

(21) Appl. No.: 17/378,434

(22) Filed: Jul. 16, 2021

(65) Prior Publication Data

US 2021/0346374 A1 Nov. 11, 2021

Related U.S. Application Data

(63) Continuation-in-part of application No. 16/337,685, filed as application No. PCT/IB2017/056009 on Sep. 29, 2017, now abandoned.

(30) Foreign Application Priority Data

Oct. 3, 2016 (IN) ............................ 201641033741

(51) Int. Cl.

*A61K 31/496* (2006.01)
*A61K 9/20* (2006.01)
*A61K 9/48* (2006.01)

(52) U.S. Cl.

CPC .......... *A61K 31/496* (2013.01); *A61K 9/2009* (2013.01); *A61K 9/2013* (2013.01); *A61K 9/2027* (2013.01); *A61K 9/2054* (2013.01); *A61K 9/485* (2013.01); *A61K 9/4858* (2013.01); *A61K 9/4866* (2013.01)

(58) Field of Classification Search

None

See application file for complete search history.

(56) References Cited

U.S. PATENT DOCUMENTS

| | | | | |
|---|---|---|---|---|
| 6,013,280 A * | 1/2000 | Frisbee | A61K 9/2077 | 424/490 |
| 7,875,605 B2 | 1/2011 | Nirogi | | |
| 8,173,637 B2 * | 5/2012 | Liu | A61K 9/2072 | 514/323 |
| 2005/0215571 A1 * | 9/2005 | Romano | A61P 39/02 | 514/259.41 |
| 2011/0053866 A1 * | 3/2011 | Duffield | A61K 9/2068 | 514/254.02 |
| 2013/0190275 A1 * | 7/2013 | Mendlovic | A61K 31/4515 | 514/154 |
| 2013/0245061 A1 * | 9/2013 | Cao | A61K 9/1694 | 264/118 |
| 2016/0324852 A1 * | 11/2016 | Friedhoff | A61K 31/445 | |

FOREIGN PATENT DOCUMENTS

| | | | |
|---|---|---|---|
| WO | 2015083179 A1 | | 6/2015 |
| WO | WO 2015/083179 | * | 6/2015 |

OTHER PUBLICATIONS

Sandeep et al. "Immediate Drug Release Dosage Form:A Review" 2013.*
Kusimi et al. "Psychopharmacology of atypical antipsychotic drugs:From the receptor binding profile to neuroprotection and neurogenesis" Oct. 2014.*
Shapiro et al. "Aripiprazole, A Novel Atypical Antispychotic Drug with a Unique and Robust Pharmacology" 2003.*
Dokic "Formulation Developement of Immediate Release Tablets Containing Fluoroquinolone Antibiotic by use of Experimental Design" abstract 2010.*
Drugband SUVN-502.*
"Discovery and Development of 1-[(2-Bromophenyl)sulfonyl]-5-methoxy-3-[(4-methyl-1-piperazinyl)methyl]-1H-indole Dimesylate Monohydrate (SUVN-502): A Novel, Potent, Selective and Orally Active Serotonin 6 (5-HT6) Receptor Antagonist for Potential Treatment" 2017.*
Vaithiananthan et al. "Effect of Common Excipients on the Oral Drug Absorption of Biopharmaceuticals Classification System Class 3 Drugs Cimetdine and Acyclovir" Feb. 2016.*
European Patent Office, "International Search Report" and "Written Opinion" issued Dec. 22, 2017 in PCT Application No. PCT/IB2017/056009.
European Patent Office, "International Report on Patentability" and its 47 page Annex including Response To Written Opinion, issued Jan. 7, 2019 in PCT Application No. PCT/IB2017/056009.
Nyol Sandeep et al., "Immediate Drug Release Dosage Form: A Review", Journal of Drug Delivery & Therapeutics, 2013, pp. 155-161.
Ichiro Kusumi et al., "Psychopharmacology of atypical antipsychotic drugs: From the receptor binding profile to neuroprotection and neurogenesis", Psychiatry and Clinical Neruosciences, Oct. 6, 2014, vol. 69; pp. 243-258.
David Shapiro et al., "Aripiprazole, A Novel Atypical Antipsychotic Drug with a Unique and Robust Pharmacology", Neuropsychopharmacology, 2003, pp. 1400-1411.
Marija Dokic et al., "Formulation Development of Immediate Release Tablets Containing Fluoroquinolone Antibiotic by use of Experimental Design", Conference Abstract from 8th Central European Symposium on Pharmaceutical Technology, 2010.

* cited by examiner

*Primary Examiner* — Danah Al-Awadi
(74) *Attorney, Agent, or Firm* — IPHORGAN LTD

(57) ABSTRACT

The present invention relates to an immediate release (IR) pharmaceutical composition comprising 1-[(2-bromophenyl)sulfonyl]-5-methoxy-3-[(4-methyl-1-piperazinyl) methyl]-1H-indole or pharmaceutically acceptable salt (s) and one or more pharmaceutically acceptable excipients. The present invention also relates to methods of preparation of said pharmaceutical compositions.

14 Claims, No Drawings

PHARMACEUTICAL COMPOSITIONS OF 5-$HT_6$ RECEPTOR ANTAGONIST

CROSS REFERENCE TO RELATED APPLICATIONS

This application is a continuation-in-part application to U.S. application Ser. No. 16/337,685, filed Mar. 28, 2019, the national state completion application of PCT Application No. PCT/IB2017/056009, filed Sep. 29, 2017, and claims priority from India Application No. 201641033741, filed Oct. 3, 2016. Each of these applications is incorporated by reference in their entirety.

FIELD OF INVENTION

The present invention relates to immediate release (IR) pharmaceutical compositions comprising 1-[(2-bromophenyl)sulfonyl]-5-methoxy-3-[(4-methyl-1-piperazinyl) methyl]-1H-indole or a pharmaceutically acceptable salt (s) thereof as an active ingredient and one or more pharmaceutically acceptable excipients and to methods of preparation of said compositions.

BACKGROUND OF INVENTION

Alzheimer's disease (AD) is the most common cause of dementia worldwide. The exponential rise in the number of cases of AD in the past and the future projection over the next few decades is anticipated to result in great pressure on the social and health-care systems of developed and developing economies alike. AD also imposes tremendous emotional and financial burden to the patient's family and community.

The compound of the present invention is a pure 5-hydroxytryptamine 6 receptor (5-$HT_6R$) antagonist with high affinity and very high selectivity over closely related serotonin receptor subtypes and improves learning and memory in animals. The 5-$HT_6R$ antagonist, 1-[(2-bromophenyl) sulfonyl]-5-methoxy-3-[(4-methyl-1-piperazinyl)methyl]-1H-indole or a pharmaceutically acceptable salt (s) thereof is described in U.S. Pat. No. 7,875,605 which is incorporated by reference.

1-[(2-Bromophenyl)sulfonyl]-5-methoxy-3-[(4-methyl-1-piperazinyl)methyl]-1H-indole dimesylate monohydrate (herein after referred to as Compound 1), which has chemical structure,

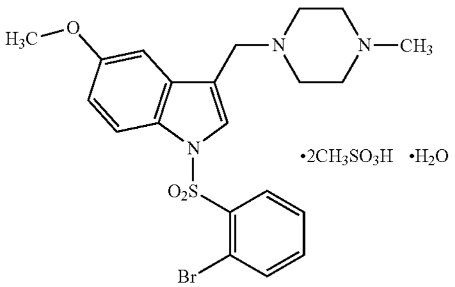

is a promising pharmaceutical active agent intended for the symptomatic treatment of Alzheimer's disease and other disorders of memory and cognition like Attention deficient hyperactivity, Parkinson's disease, schizophrenia, lewy body dementia, vascular dementia or frontotemporal dementia. The process for preparing compound 1 on a larger scale is described in WO2015083179A1.

There is a need to develop a suitable dosage form of the compound 1 to treat the patients with AD and other disorders of memory and cognition like Attention deficient hyperactivity, Parkinson's disease, schizophrenia, lewy body dementia, vascular dementia or frontotemporal dementia. In our present invention, we developed IR pharmaceutical compositions of compound 1 having (1) excellent properties of tablet formation, (2) excellent wetting, disintegration, rapid and complete drug release properties, (3) good purity profile and (4) stable formulation for the treatment of AD and other disorders of memory and cognition like Attention deficient hyperactivity, Parkinson's disease, schizophrenia, lewy body dementia, vascular dementia or frontotemporal dementia.

SUMMARY OF INVENTION

In one aspect, the present invention relates to immediate release pharmaceutical composition comprising 1-[(2-bromophenyl)sulfonyl]-5-methoxy-3-[(4-methyl-1-piperazinyl) methyl]-1H-indole or a pharmaceutically acceptable salt thereof and one or more pharmaceutically acceptable excipients.

In another aspect, the present invention relates to immediate release pharmaceutical composition comprising 1-[(2-bromophenyl)sulfonyl]-5-methoxy-3-[(4-methyl-1-piperazinyl) methyl]-1H-indole dimesylate monohydrate and one or more pharmaceutically acceptable excipients.

In another aspect, the present invention relates to immediate release pharmaceutical composition comprising 1-[(2-bromophenyl)sulfonyl]-5-methoxy-3-[(4-methyl-1-piperazinyl) methyl]-1H-indole dimesylate monohydrate, wherein the pharmaceutical composition comprises binder, diluent, lubricant, glidant, and disintegrant.

In another aspect, the present invention relates to immediate release pharmaceutical composition comprising, a) 1-[(2-bromophenyl)sulfonyl]-5-methoxy-3-[(4-methyl-1-piperazinyl) methyl]-1H-indole or a pharmaceutically acceptable salt thereof;
b) diluent;
c) lubricant; and
d) glidant.

In another aspect, the present invention relates to immediate release pharmaceutical composition comprising, a) 1-[(2-bromophenyl)sulfonyl]-5-methoxy-3-[(4-methyl-1-piperazinyl) methyl]-1H-indole or a pharmaceutically acceptable salt thereof;
b) diluent;
c) lubricant;
d) glidant; and
e) disintegrant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole or a pharmaceutically acceptable salt thereof, wherein said composition comprises on a total of 100% by weight:

(a) from about 2% to about 60% 1-[(2-bromophenyl) sulfonyl]-5-methoxy-3-[(4-methyl-1-piperazinyl) methyl]-1H-indole dimesylate monohydrate;
(b) from about 36% to about 97% diluent;
(c) from about 0.5% to about 2% lubricant;
(d) from about 0.5% to about 1% glidant;
(e) 0% to about 10% binder; and
(f) 0% to about 5% disintegrant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 2% to about 60% 1-[(2-bromophenyl) sulfonyl]-5-methoxy-3-[(4-methyl-1-piperazinyl) methyl]-1H-indole dimesylate monohydrate;
(b) from about 36% to about 97% diluent;
(c) from about 0.5% to about 2% lubricant;
(d) from about 0.5% to about 1% glidant;
(e) 0% to about 10% binder; and
(f) 0% to about 5% disintegrant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 2% to about 3% 1-[(2-bromophenyl) sulfonyl]-5-methoxy-3-[(4-methyl-1-piperazinyl) methyl]-1H-indole dimesylate monohydrate;
(b) about 95% to about 97% diluent;
(c) about 1% lubricant; and
(d) about 0.5% glidant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 11% to about 38% 1-[(2-bromophenyl) sulfonyl]-5-methoxy-3-[(4-methyl-1-piperazinyl) methyl]-1H-indole dimesylate monohydrate;
(b) from about 61% to about 87% of diluent;
(c) from about 1% to about 2% lubricant; and
(d) about 0.5% glidant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 48% to about 60% 1-[(2-bromophenyl) sulfonyl]-5-methoxy-3-[(4-methyl-1-piperazinyl) methyl]-1H-indole dimesylate monohydrate;
(b) about 38% to about 48% diluent;
(c) about 1% lubricant; and
(d) about 0.5% glidant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 12% to about 18% 1-[(2-bromophenyl) sulfonyl]-5-methoxy-3-[(4-methyl-1-piperazinyl) methyl]-1H-indole dimesylate monohydrate;
(b) from about 78% to about 86% diluent;
(c) about 1% lubricant;
(d) about 0.5% glidant; and
(e) about 2% disintegrant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 24% to about 38% 1-[(2-bromophenyl) sulfonyl]-5-methoxy-3-[(4-methyl-1-piperazinyl) methyl]-1H-indole dimesylate monohydrate;
(b) from about 61% to about 72% diluent;
(c) from about 1% to about 1.25% lubricant;
(d) about 0.5% glidant; and
(e) from about 0.5 to about 2% disintegrant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 36% to about 60% 1-[(2-bromophenyl) sulfonyl]-5-methoxy-3-[(4-methyl-1-piperazinyl) methyl]-1H-indole dimesylate monohydrate;
(b) from about 36% to about 62% diluent;
(c) from about 0.5% to about 1% lubricant;
(d) about 0.5% glidant; and
(e) about 2% disintegrant.

In yet another aspect, the present invention relates to immediate release pharmaceutical composition of 1-[(2-bromophenyl)sulfonyl]-5-methoxy-3-[(4-methyl-1-piperazinyl) methyl]-1H-indole dimesylate monohydrate, wherein said composition comprises on a total of 100% by weight:

(a) from about 11% to about 38% 1-[(2-bromophenyl) sulfonyl]-5-methoxy-3-[(4-methyl-1-piperazinyl) methyl]-1H-indole dimesylate monohydrate;
(b) from about 61% to about 72% diluent;
(c) about 1% lubricant;
(d) from about 2% to about 10% binder;
(e) about 0.5% glidant; and
(f) from about 2% to about 5% disintegrant.

In yet another aspect, the present invention also relates to methods of preparation of immediate release pharmaceutical compositions.

In yet another aspect the present invention relates to an immediate release tablet, wherein said tablet comprises on a total of 100% by weight:

(a) from about 2% to about 60% 1-[(2-bromophenyl) sulfonyl]-5-methoxy-3-[(4-methyl-1-piperazinyl) methyl]-1H-indole dimesylate monohydrate;
(b) from about 36% to about 97% diluent;
(c) 0% to about 10% binder;
(d) from about 0.5% to about 2% lubricant;
(e) from about 0.5% to about 1% glidant; and
(f) 0% to about 5% disintegrant.

In yet another aspect, the present invention relates to immediate release tablet, wherein said tablet comprises on a total of 100% by weight:

(a) from about 2% to about 3% 1-[(2-bromophenyl) sulfonyl]-5-methoxy-3-[(4-methyl-1-piperazinyl) methyl]-1H-indole dimesylate monohydrate;
(b) about 95% to about 97% diluent;
(c) about 1% lubricant; and
(d) about 0.5% glidant.

In yet another aspect, the present invention relates to immediate release tablet, wherein said tablet comprises on a total of 100% by weight:

(a) from about 11% to about 38% 1-[(2-bromophenyl) sulfonyl]-5-methoxy-3-[(4-methyl-1-piperazinyl) methyl]-1H-indole dimesylate monohydrate;
(b) from about 61% to about 87% diluent;
(c) from about 1% to about 2% lubricant; and
(d) about 0.5% glidant.

In yet another aspect, the present invention relates to immediate release tablet, wherein said tablet comprises on a total of 100% by weight:

(a) from about 48% to about 60% 1-[(2-bromophenyl) sulfonyl]-5-methoxy-3-[(4-methyl-1-piperazinyl) methyl]-1H-indole dimesylate monohydrate;
(b) about 38% to about 48% diluent;
(c) about 1% lubricant; and
(d) about 0.5% glidant.

In yet another aspect, the present invention relates to immediate release tablet, wherein said tablet comprises on a total of 100% by weight:

(a) from about 12% to about 18% 1-[(2-bromophenyl) sulfonyl]-5-methoxy-3-[(4-methyl-1-piperazinyl) methyl]-1H-indole dimesylate monohydrate;
(b) from about 78% to about 86% diluent;
(c) about 1% lubricant;
(d) about 0.5% glidant; and
(e) about 2% disintegrant.

In yet another aspect, the present invention relates to immediate release tablet, wherein tablet comprises on a total of 100% by weight:

(a) from about 24% to about 38% 1-[(2-bromophenyl) sulfonyl]-5-methoxy-3-[(4-methyl-1-piperazinyl) methyl]-1H-indole dimesylate monohydrate;
(b) from about 61% to about 72% diluent;
(c) from about 1% to about 1.25% lubricant;
(d) about 0.5% glidant; and
(e) from about 0.5% to about 2% disintegrant.

In yet another aspect, the present invention relates to immediate release tablet, wherein said tablet comprises on a total of 100% by weight:

(a) from about 36% to about 60% 1-[(2-bromophenyl) sulfonyl]-5-methoxy-3-[(4-methyl-1-piperazinyl) methyl]-1H-indole dimesylate monohydrate;
(b) from about 36% to about 62% diluent;
(c) from about 0.5% to about 1% lubricant;
(d) about 0.5% glidant; and
(e) about 2% disintegrant.

In yet another aspect, the present invention relates to immediate release tablet, wherein said tablet comprises on a total of 100% by weight:

(a) from about 11% to about 38% 1-[(2-bromophenyl) sulfonyl]-5-methoxy-3-[(4-methyl-1-piperazinyl) methyl]-1H-indole dimesylate monohydrate;
(b) from about 61% to about 72% diluent;
(c) about 1% lubricant;
(d) from about 2% to about 10% binder;
(e) about 0.5% glidant; and
(f) from about 2% to about 5% disintegrant.

In yet another aspect, the present invention relates to the immediate release pharmaceutical composition of dose ranges from about 5 mg to about 200 mg.

In yet another aspect, the present invention relates to the immediate release pharmaceutical composition, wherein the total weight of the immediate release tablet is from about 100 mg to about 600 mg.

In yet another aspect, the present invention relates to the immediate release pharmaceutical composition, wherein the immediate release pharmaceutical composition comprises, i) less than 0.5% of chloro impurity;
ii) less than 0.5% of unknown impurity;
iii) less than 1% of total impurity.

In yet another aspect, the present invention relates to the immediate release pharmaceutical composition, wherein the purity of the 1-[(2-bromophenyl)sulfonyl]-5-methoxy-3-[(4-methyl-1-piperazinyl) methyl]-1H-indole dimesylate monohydrate is about 99.3%.

In yet another aspect, the present invention relates to the immediate release pharmaceutical composition, wherein the 1-[(2-bromophenyl)sulfonyl]-5-methoxy-3-[(4-methyl-1-piperazinyl) methyl]-1H-indole dimesylate monohydrate is released about 85% to about 100% within 30 minutes.

DETAILED DESCRIPTION OF INVENTION

Unless otherwise stated, the following terms used in the specification and claims have the meanings given below:

The term, "pharmaceutically acceptable excipients" as used herein refers to diluents, disintegrants, binders, lubricants, glidants, polymers, coating agents, solvents, co-solvents, preservatives, wetting agents, thickening agents, anti-foaming agents, sweetening agents, flavouring agents, antioxidants, colorants, solubulizers, plasticizer or dispersing agents and the like. The pharmaceutical compositions of the present invention may be formulated in a conventional manner using one or more pharmaceutically acceptable excipients.

The "binder" employed in a composition of the present invention is capable for holding the ingredients together and forming the granules with required mechanical strength. Example of binders includes without limitation, polyvinylpyrrolidone (povidone (PVPK30)), polyethlylene glycol (PEG), saccharides, gelatins, pregelatinized starches, hydroxypropylcellulose, hydroxypropyl methylcellulose (HPMC) and cellulose ethers.

The "diluent" employed in a composition of the present invention is capable for providing bulkiness to obtain a desired immediate release pharmaceutical composition. Preferred diluents are inorganic phosphates such as dibasic calcium phosphate, calcium sulphate or dicalcium phosphate dihydrate; sugars such as lactose, lactose hydrate, lactose monohydrate, lactose anhydrate, sucrose, dextrose, erythritol, lactilol, xylitol, sorbitol, mannitol or malitol; cellulose or cellulose derivatives such as microcrystalline cellulose; Avicel, Avicel PH 101, Avicel PH 102 or Avicel PH 103, maize starch, Starcap-1500, Starlac and isomalt (galenIQ-721).

The "disintegrant" employed in a composition of the present invention is capable of facilitating the breakup of an immediate release pharmaceutical composition prepared from the composition when placed in contact with an aqueous medium. Preferred disintegrants are alginic acid or sodium alginate; cellulose or cellulose derivatives such as carboxymethylcellulose sodium, croscarmellose sodium, powdered cellulose or croscarmellose; iron exchange resin such as amberlite, gums such as agar, locust bean, karaya, pectin and tragacanth, crospovidone (cross-linked homopolymer of N-vinyl-2-pyrrolidinone, i.e., cross-linked 1-ethenyl-2-pyrrolidinone); sodium starch glycolate or starch.

The "lubricant" employed in a composition of the present invention is capable of preventing the ingredients from clumping together and from sticking to the apparatus on which it is formed, for example, preventing adherence to the face of the upper punch (picking) or lower punch (sticking) of a compression machine. Preferred lubricants are fatty acids or fatty acid derivatives such as calcium stearate, glyceryl monostearate, glyceryl palmitostearate, talc, magnesium stearate, sodium lauryl sulfate, sodium stearyl fumarate, zinc stearate, stearic acid or hydrogenated vegetable oil; polyalkylene glycols such as polyethylene glycol (PEG) or sodium benzoate and the like.

The "glidant" employed in a composition of the present invention is capable for increase in flow, those selected from the group consisting of colloidal silicon dioxide (Aerosil), higher fatty acids, the metal salts, talc, and the like or the mixtures thereof.

The "coloring agent" (or "colorant") employed in a composition of the present invention may be one or more compounds which impart a desired color to the composition. Addition of a coloring agent may be used, for example, so that tablets of different potencies may be easily distinguished. Example of coloring agent includes but not limited to beta-carotene, indigo carmine, sunset yellow FCF, tartrazine, brilliant blue FCF, titanium dioxide, quinoline yellow, allura red AC, quinizarine green SS and iron oxides, which are accepted universally.

The "active ingredient" defined in this invention is 1-[(2-bromophenyl)sulfonyl]-5-methoxy-3-[(4-methyl-1-piperazinyl)methyl]-1H-indole dimesylate monohydrate.

The term "about" means within an acceptable error range for the particular value as determined by one of ordinary skill in the art, which will depend in part on how the value is measured or determined, i.e., the limitations of the measurement system. The term "about" as used herein refers to a defined range of the value by ±10%. For example, about 2% means 1.8% to 2.2%, about 5% means 4.5% to 5.5%, about 10% means 9% to 11% and about 40% means 36% to 44%.

The term, "pharmaceutically acceptable salt" as used herein refers to salts of the active ingredient and are prepared by reaction with the appropriate acid or acid derivative, depending on the particular substituents found on the compounds described herein. The pharmaceutically acceptable salt includes but not limited to dimesylate monohydrate salt, dihydrochloride salt, oxalate salt, tartrate salt and the like. Preferably, the pharmaceutically acceptable salt is dimesylate monohydrate salt and dihydrochloride salt. More preferably, the pharmaceutically acceptable salt is dimesylate monohydrate salt.

The term, "patient" as used herein refers to an animal. Preferably the term "patient" refers to mammal. The term mammal includes animals such as mice, rats, dogs, rabbits, pigs, monkeys, horses and human. More preferably the patient is human.

The term "impurity" as used herein refers to any component of a drug substance that is not the chemical entity defined as the drug substance and in addition, for a drug product, any component that is not a formulation ingredient.

The term, "immediate release composition" refers to a composition of an active ingredient which disintegrates rapidly and releases greater than 85% at 30 minutes.

The immediate release pharmaceutical compositions of the present invention can be used for treatment or prevention of Alzheimer's disease and other disorders of memory and cognition like Attention deficient hyperactivity, Parkinson's disease, schizophrenia, lewy body dementia, vascular dementia or frontotemporal dementia. The immediate release pharmaceutical composition of the instant invention can be administered orally, in an effective amount, to a mammalian (especially human) subject to treat or prevent the aforementioned disorders.

The effective dosage of the immediate release pharmaceutical composition comprising 1-[(2-bromophenyl)sulfonyl]-5-methoxy-3-[(4-methyl-1-piperazinyl) methyl]-1H-indole dimesylate monohydrate is about 5 mg to about 200 mg. The immediate release pharmaceutical composition can be administered 1 to 3 times per day, based on condition of the patients. The total weight of immediate release pharmaceutical composition of the present invention is from about 100 mg to 600 mg.

The compound 1 belongs to class I as per BCS classification based on our experimental results and hence particle size of the compound 1 does not effect in the treatment of the patient.

In one embodiment the present invention relates to the immediate release pharmaceutical composition comprising:

| Ingredient | Range (% w/w) | Preferred Range (% w/w) |
|---|---|---|
| Compound 1 (Active ingredient) | 2-60 | 10-50 |
| Diluent | 36-97 | 40-90 |
| Binder | 0-10 | 3-5 |
| Disintegrant | 0-5 | 2-4 |
| Lubricant | 0.5-2 | 0.5-1 |
| Glidant | 0.5-1 | 0.5-1 |

In yet another embodiment, the present invention relates to the immediate release pharmaceutical composition comprises about 2% to about 3% by weight of 1-[(2-bromophenyl)sulfonyl]-5-methoxy-3-[(4-methyl-1-piperazinyl) methyl]-1H-indole dimesylate monohydrate.

In yet another embodiment, the present invention relates to the immediate release pharmaceutical composition comprises about 10% to about 40% by weight of 1-[(2-bromophenyl)sulfonyl]-5-methoxy-3-[(4-methyl-1-piperazinyl) methyl]-1H-indole dimesylate monohydrate.

In yet another embodiment, the present invention relates to the immediate release pharmaceutical composition comprises about 20% to about 40% by weight of 1-[(2-bromophenyl)sulfonyl]-5-methoxy-3-[(4-methyl-1-piperazinyl) methyl]-1H-indole dimesylate monohydrate.

In yet another embodiment, the present invention relates to the immediate release pharmaceutical composition comprises about 30% to about 50% by weight of 1-[(2-bromophenyl)sulfonyl]-5-methoxy-3-[(4-methyl-1-piperazinyl) methyl]-1H-indole dimesylate monohydrate.

In yet another embodiment, the present invention relates to the immediate release pharmaceutical composition comprises about 30% to about 60% by weight of 1-[(2-bromophenyl)sulfonyl]-5-methoxy-3-[(4-methyl-1-piperazinyl) methyl]-1H-indole dimesylate monohydrate.

In yet another embodiment, the present invention relates to the immediate release pharmaceutical composition comprising about 40% to about 80% by weight of diluent.

In yet another embodiment, the present invention relates to the immediate release pharmaceutical composition comprising about 70% to about 90% by weight of diluent.

In yet another embodiment, the present invention relates to the immediate release pharmaceutical composition comprising about 20% to about 40% by weight of diluent.

In yet another embodiment, the present invention relates to the immediate release pharmaceutical composition in the form of tablet or capsule.

In yet another embodiment, the present invention relates to an immediate release tablet, wherein the tablet comprises, (a) from about 2% to about 60% 1-[(2-bromophenyl) sulfonyl]-5-methoxy-3-[(4-methyl-1-piperazinyl) methyl]-1H-indole dimesylate monohydrate;
(b) from about 36% to about 97% microcrystalline cellulose;
(c) from about 0.5% to about 2% magnesium stearate; and
(d) from about 0.5% to about 1% colloidal silicon dioxide.

In yet another embodiment, the present invention relates to an immediate release tablet, wherein the tablet comprises, (a) from about 2% to about 60% 1-[(2-bromophenyl) sulfonyl]-5-methoxy-3-[(4-methyl-1-piperazinyl) methyl]-1H-indole dimesylate monohydrate;
(b) from about 36% to about 97% microcrystalline cellulose;
(c) from about 0.5% to about 2% magnesium stearate;
(d) from about 0.5% to about 1% colloidal silicon dioxide; and
(e) from about 0.5% to about 5% crospovidone.

In yet another embodiment, the present invention relates to an immediate release tablet, wherein the tablet comprises, (a) from about 2% to about 60% 1-[(2-bromophenyl) sulfonyl]-5-methoxy-3-[(4-methyl-1-piperazinyl) methyl]-1H-indole dimesylate monohydrate;
(b) from about 36% to about 97% microcrystalline cellulose;
(c) from about 0.5% to about 2% magnesium stearate;
(d) from about 0.5% to about 1% colloidal silicon dioxide;
(e) 0% to about 10% povidone; and
(f) 0% to about 5% crospovidone.

In yet another embodiment, the present invention relates to an immediate release tablet, wherein the tablet comprises, (a) from about 20% to about 50% 1-[(2-bromophenyl) sulfonyl]-5-methoxy-3-[(4-methyl-1-piperazinyl) methyl]-1H-indole dimesylate monohydrate;
(b) from about 40% to about 75% microcrystalline cellulose;
(c) from about 0.5% to about 2% magnesium stearate;
(d) from about 0.5% to about 1% colloidal silicon dioxide; and
(f) from about 0.5% to about 2% crospovidone.

In yet another embodiment, the present invention relates to the immediate release pharmaceutical composition comprises about 40% to about 80% by weight of microcrystalline cellulose.

In yet another embodiment, the present invention relates to the immediate release pharmaceutical composition comprises about 70% to about 90% by weight of microcrystalline cellulose.

In yet another embodiment, the present invention relates to the immediate release pharmaceutical composition comprises about 20% to about 40% by weight of microcrystalline cellulose.

In yet another embodiment, the present invention relates to the immediate release pharmaceutical composition comprises from 0.5% to about 2% by weight of crospovidone.

In yet another embodiment, the present invention relates to the immediate release pharmaceutical composition comprises about 4% by weight of povidone.

In other aspect, the present invention relates to the use of the immediate release pharmaceutical composition comprising 1-[(2-bromophenyl)sulfonyl]-5-methoxy-3-[(4-methyl-1-piperazinyl) methyl]-1H-indole or a pharmaceutically acceptable salt thereof and one or more pharmaceutically acceptable excipients for the treatment of Alzheimer's disease, memory and cognition disorders selected from Attention deficient hyperactivity disorder, Parkinson's disease, schizophrenia, lewy body dementia, vascular dementia or frontotemporal dementia.

In yet another aspect, the instant invention relates to the method of treatment of Alzheimer's disease, memory and cognition disorders selected from Attention deficient hyperactivity disorder, Parkinson's disease, schizophrenia, lewy body dementia, vascular dementia or frontotemporal dementia comprising administering to a patient a therapeutically effective amount of the immediate release pharmaceutical composition comprising 1-[(2-bromophenyl)sulfonyl]-5-methoxy-3-[(4-methyl-1-piperazinyl) methyl]-1H-indole or a pharmaceutically acceptable salt thereof and one or more pharmaceutically acceptable excipients.

Methods of Preparation of Immediate Release Pharmaceutical Composition

In another aspect, the instant invention relates to the process for the preparation of the immediate release pharmaceutical composition comprising 1-[(2-bromophenyl) sulfonyl]-5-methoxy-3-[(4-methyl-1-piperazinyl) methyl]-1H-indole or a pharmaceutically acceptable salt thereof.

The preparation of the immediate release pharmaceutical composition includes two methods, a) direct compression method and b) wet granulation method.

In one embodiment, the preparation of the immediate release pharmaceutical composition using direct compression method comprises the following steps:

a) weighing the active ingredient and diluent and sieving through sieve number 40;
b) mixing the sieved active ingredient and diluent;
c) weighing the lubricant, glidant, disintegrant and sieving through sieve number 40;
d) adding the mixture obtained in step (c) into step (b) and blending the mixture for 5-20 minutes to form homogenous mixture; and
e) compressing the lubricated blend to obtain the required dosage form.

The above obtained dosage forms can be optionally coated with polymers, solvents and coloring agents by methods known in the art.

In another embodiment, the preparation of the immediate release pharmaceutical composition using wet granulation method comprises the following steps:

a) weighing the active ingredient, diluent and disintegrant;
b) sieving the weighed materials through sieve number 40;
c) blending the sieved active ingredient, diluent and disintegrant for 10 minutes in an octagonal blender;
d) weighing the binder and dissolve in required quantity of purified water;
e) transferring the active ingredient, diluent and disintegrant into RMG;
f) adding binder solution dropwise to RMG to form cohesive mass;
g) drying the blend in a tray drier at 50° C.;
h) passing the blend through #18 mesh to form granules;
i) weighing the lubricant and glidant and pass through sieve number 40;
j) adding the mixture obtained in step (h) to step (i) and blend for 10 minutes in an octagonal blender; and
k) compressing the lubricated blend to obtain the required dosage form.

The above obtained dosage forms can be optionally coated with polymers, solvents and coloring agents by methods known in the art.

ABBREVIATIONS

AUC Area under the curve
$C_{max}$ Maximum plasma concentration
HDPE High density polyethylene
HPMC Hydroxypropyl methylcellulose
HPLC High performance liquid chromatography
kg Kilogram LC-MS/MS Liquid chromatography/Tandem mass spectrometry
mg Milligram
mL Milliliter
ng Nanogram
N Normality
rpm Rotation per minute
RMG Rapid mixer granulator
$T_{max}$ Time of maximum plasma concentration
$T_{1/2}$ Half-life
° C. Degree Celsius
% W/W Percent weight/weight
UV Ultra violet

EXAMPLES

The following Examples are provided to illustrate preferred embodiments of the invention and are not intended to limit the scope of the present invention.

Example 1: Pharmaceutical Composition of Compound 1 IR Tablets

By using range of ingredients (% w/w) in below mentioned table and procedures explained in above mentioned preparation methods, the IR tablets of 1-[(2-bromophenyl) sulfonyl]-5-methoxy-3-[(4-methyl-1-piperazinyl)methyl]-1H-indole dimesylate monohydrate are prepared.

| Ingredient | Range (% w/w) |
|---|---|
| Compound 1 | 2-60 |
| Binder | 0-5 |
| Diluent | 36-97 |
| Disintegrant | 0-4 |
| Lubricant | 0.5-2 |
| Glidant | 0.5-1 |

Example 2

Preparation of IR Tablet Using Direct Compression Method: Composition of 5 mg Dose IR Tablet:

| Ingredient | % w/w | mg/tablet |
|---|---|---|
| Compound 1 | 2.47 | 7.41# |
| Microcrystalline cellulose (Avicel PH 102) | 96.03 | 288.09 |
| Magnesium stearate | 1 | 3 |
| Colloidal silicon dioxide (Aerosil ®) | 0.5 | 1.5 |
| Total | 100 | 300 |

#equivalent to 5 mg of 1-[(2-bromophenyl)sulfonyl]-5-methoxy-3-[(4-methyl-1-piperazinyl) methyl]-1H-indole (free base compound).

Method of Preparing IR Tablet:

All the ingredients were accurately weighed (Compound 1 of 2.47%, Avicel PH 102 of 96.03%) and sieved using sieve number 40. The sieved compound 1 and Avicel PH 102 were blended for 10 minutes in an octagonal blender. The mixture obtained was added to magnesium stearate (1%) and aerosil (0.5%) and blended for 10 minutes in an octagonal blender. The lubricated blend was compressed using 9 mm round concave punches and dies on rotary compression machine to obtain 300 mg tablet.

The examples 3 to 46 were prepared by following the method of preparation of example 2 by using appropriate amount of active ingredient, diluent, disintegrant, lubricant, and glidant.

Examples 3 to 11

Compositions of 25 mg Dose IR Tablets:

| | Example 3 | | Example 4 | |
|---|---|---|---|---|
| Ingredient | (% w/w) | mg/tablet | (% w/w) | mg/tablet |
| Compound 1 | 12.34 | 37.02# | 14.81 | 37.02# |
| Microcrystalline cellulose (Avicel PH 102) | 86.16 | 258.48 | 83.69 | 209.23 |
| Magnesium stearate | 1 | 3 | 1 | 2.5 |
| Colloidal silicon dioxide (Aerosil ®) | 0.5 | 1.5 | 0.5 | 1.25 |
| Total | 100 | 300 | 100 | 250 |

#equivalent to 25 mg of 1-[(2-bromophenyl)sulfonyl]-5-methoxy-3-[(4-methyl-1-piperazinyl) methyl]-1H-indole (free base compound)

| | Example 5 | | Example 6 | |
|---|---|---|---|---|
| Ingredient | (% w/w) | mg/tablet | (% w/w) | mg/tablet |
| Compound 1 | 37.03 | 37.03# | 12.42 | 37.26# |
| Microcrystalline cellulose (Avicel PH 102) | 61.47 | 61.47 | 84.08 | 252.24 |
| Magnesium stearate | 1 | 1 | 1 | 3 |
| Colloidal silicon dioxide (Aerosil ®) | 0.5 | 0.5 | 0.5 | 1.5 |
| Crospovidone | — | — | 2 | 6 |
| Total | 100 | 100 | 100 | 300 |

#equivalent to 25 mg of 1-[(2-bromophenyl)sulfonyl]-5-methoxy-3-[(4-methyl-1-piperazinyl) methyl]-1H-indole (free base compound)

| | Example 7 | | Example 8 | |
|---|---|---|---|---|
| Ingredient | (% w/w) | mg/tablet | (% w/w) | mg/tablet |
| Compound 1 | 16.93 | 37.25# | 16.93 | 37.25# |
| Microcrystalline cellulose (Avicel PH 102) | 79.57 | 175.05 | 81.57 | 179.45 |
| Magnesium stearate | 1 | 2.2 | 1 | 2.2 |
| Colloidal silicon dioxide (AerosiH) | 0.5 | 1.1 | 0.5 | 1.1 |
| Crospovidone | 2 | 4.4 | — | — |
| Total | 100 | 220 | 100 | 220 |

#equivalent to 25 mg of 1-[(2-bromophenyl)sulfonyl]-5-methoxy-3-[(4-methyl-1-piperazinyl) methyl]-1H-indole (free base compound)

| | Example 9 | | Example 10 | |
|---|---|---|---|---|
| Ingredient | (% w/w) | mg/tablet | (% w/w) | mg/tablet |
| Compound 1 | 16.93 | 37.25# | 16.93 | 37.25# |
| Microcrystalline cellulose (Avicel PH 102) | — | — | 81.57 | 179.45 |
| Dibasic calcium phosphate dihydrate | 81.57 | 179.45 | — | — |

-continued

| Ingredient | Example 9 (% w/w) | Example 9 mg/tablet | Example 10 (% w/w) | Example 10 mg/tablet |
|---|---|---|---|---|
| Magnesium stearate | 1 | 2.2 | 1 | 2.2 |
| Colloidal silicon dioxide (Aerosil ®) | 0.5 | 1.1 | 0.5 | 1.1 |
| Total | 100 | 220 | 100 | 220 |

#equivalent to 25 mg of 1-[(2-bromophenyl)sulfonyl]-5-methoxy-3-[(4-methyl-1-piperazinyl) methyl]-1H-indole (free base compound)

| Ingredient | Example 11 (% w/w) | Example 11 mg/tablet |
|---|---|---|
| Compound 1 | 16.93 | 37.25# |
| Starch (Starlac) | 81.57 | 179.45 |
| Magnesium stearate | 1 | 2.2 |
| Colloidal silicon dioxide (Aerosil ®) | 0.5 | 1.1 |
| Total | 100 | 220 |

#equivalent to 25 mg of 1-[(2-bromophenyl)sulfonyl]-5-methoxy-3-[(4-methyl-1-piperazinyl) methyl]-1H-indole (free base compound)

Examples 12 to 33

Compositions of 50 mg Dose IR Tablets:

| Ingredient | Example 12 (% w/w) | Example 12 mg/tablet | Example 13 (% w/w) | Example 13 mg/tablet |
|---|---|---|---|---|
| Compound 1 | 29.62 | 74.05# | 29.62 | 74.05# |
| Microcrystalline cellulose (Avicel PH 102) | 66.63 | 166.58 | — | — |
| Isomalt | — | — | 68.88 | 172.2 |
| Magnesium stearate | 1.25 | 3.12 | 1 | 2.5 |
| Colloidal silicon dioxide (Aerosil ®) | 0.5 | 1.25 | 0.5 | 1.25 |
| Crospovidone | 2 | 5 | — | — |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| Ingredient | Example 14 (% w/w) | Example 14 mg/tablet | Example 15 (% w/w) | Example 15 mg/tablet |
|---|---|---|---|---|
| Compound 1 | 29.62 | 74.05# | 28.8 | 72# |
| Starch (Starlac) | 68.88 | 172.2 | — | — |
| Microcrystalline cellulose (Avicel PH 113) | — | — | 69.45 | 173.63 |
| Magnesium stearate | 1 | 2.5 | 1.25 | 3.12 |
| Colloidal silicon dioxide (Aerosil ®) | 0.5 | 1.25 | 0.5 | 1.25 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| Ingredient | Example 16 (% w/w) | Example 16 mg/tablet | Example 17 (% w/w) | Example 17 mg/tablet |
|---|---|---|---|---|
| Compound 1 | 28.8 | 72# | 29.62 | 74.05# |
| Microcrystalline cellulose (Avicel PH 102) | 69.45 | 173.63 | — | — |
| Lactose Monohydrate | — | — | 68.63 | 171.58 |
| Magnesium stearate | 1.25 | 3.12 | 1.25 | 3.12 |
| Colloidal silicon dioxide (Aerosil ®) | 0.5 | 1.25 | 0.5 | 1.25 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| Ingredient | Example 18 (% w/w) | Example 18 mg/tablet | Example 19 (% w/w) | Example 19 mg/tablet |
|---|---|---|---|---|
| Compound 1 | 29.62 | 74.05# | 28.8 | 72# |
| Starch (Starcap 1500) | 68.63 | 171.58 | — | — |
| Microcrystalline cellulose (Avicel PH 101) | — | — | 69.45 | 173.63 |
| Magnesium stearate | 1.25 | 3.12 | 1.25 | 3.12 |
| Colloidal silicon dioxide (Aerosil ®) | 0.5 | 1.25 | 0.5 | 1.25 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| Ingredient | Example 20 (% w/w) | Example 20 mg/tablet | Example 21 (% w/w) | Example 21 mg/tablet |
|---|---|---|---|---|
| Compound 1 | 29.62 | 74.05# | 29.62 | 74.05# |
| Dextrose Monohydrate | 68.88 | 172.2 | — | — |
| Mannitol | — | — | 68.88 | 172.2 |
| Magnesium stearate | 1 | 2.5 | 1 | 2.5 |
| Colloidal silicon dioxide (Aerosil ®) | 0.5 | 1.25 | 0.5 | 1.25 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| Ingredient | Example 22 (% w/w) | Example 22 mg/tablet | Example 23 (% w/w) | Example 23 mg/tablet |
|---|---|---|---|---|
| Compound 1 | 37.03 | 74.06# | 29.62 | 74.05# |
| Microcrystalline cellulose (Avicel PH 102) | 61.47 | 122.94 | — | — |
| Dicalcium phosphate dihydrate | — | — | 68.63 | 171.58 |
| Magnesium stearate | 1 | 2 | 1.25 | 3.12 |
| Colloidal silicon dioxide (Aerosil ®) | 0.5 | 1 | 0.5 | 1.25 |
| Total | 100 | 200 | 100 | 250 |

#equivalent to 50 mg of 1-[(2-bromophenyl)sulfonyl]-5-methoxy-3-[(4-methyl-1-piperazinyl) methyl]-1H-indole (free base compound)

| | Example 24 | | Example 25 | |
|---|---|---|---|---|
| Ingredient | (% w/w) | mg/tablet | (% w/w) | mg/tablet |
| Compound 1 | 29.62 | 74.05# | 29.62 | 74.05# |
| Microcrystalline cellulose (Avicel PH 101) | 68.63 | 171.58 | — | — |
| Lactose Monohydrate | — | — | 66.63 | 166.58 |
| Magnesium stearate | 1.25 | 3.12 | 1.25 | 3.12 |
| Colloidal silicon dioxide (Aerosil ®) | 0.5 | 1.25 | 0.5 | 1.25 |
| Crospovidone | — | — | 2 | 5 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| | Example 26 | | Example 27 | |
|---|---|---|---|---|
| Ingredient | (% w/w) | mg/tablet | (% w/w) | mg/tablet |
| Compound 1 | 29.62 | 74.05# | 29.62 | 74.05# |
| Starch (Starcap 1500) | — | — | 66.63 | 166.58 |
| Dicalcium phosphate dihydrate | 66.63 | 166.58 | — | — |
| Magnesium stearate | 1.25 | 3.12 | 1.25 | 3.12 |
| Colloidal silicon dioxide (Aerosil ®) | 0.5 | 1.25 | 0.5 | 1.25 |
| Crospovidone | 2 | 5 | 2 | 5 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| | Example 28 | | Example 29 | |
|---|---|---|---|---|
| Ingredient | (% w/w) | mg/tablet | (% w/w) | mg/tablet |
| Compound 1 | 29.62 | 74.05# | 29.62 | 74.05# |
| Lactose Monohydrate | 66.63 | 166.58 | — | — |
| Microcrystalline cellulose (Avicel 101) | — | — | 66.63 | 166.58 |
| Magnesium stearate | 1.25 | 3.12 | 1.25 | 3.12 |
| Colloidal silicon dioxide (Aerosil ®) | 0.5 | 1.25 | 0.5 | 1.25 |
| Crospovidone | 2 | 5 | 2 | 5 |
| Total | 100 | 250 | 100 | 250 |

#equivalent to 50 mg of 1-[(2-bromophenyl)sulfonyl]-5-methoxy-3-[(4-methyl-1-piperazinyl) methyl]-1H-indole (free base compound)

| | Example 30 | | Example 31 | |
|---|---|---|---|---|
| Ingredient | (% w/w) | mg/tablet | (% w/w) | mg/tablet |
| Compound 1 | 24.83 | 74.5# | 33.86 | 74.5# |
| Microcrystalline cellulose (Avicel PH 102) | 71.67 | 215 | 62.64 | 137.8 |
| Magnesium stearate | 1 | 3 | 1 | 2.2 |
| Colloidal silicon dioxide (Aerosil ®) | 0.5 | 1.5 | 0.5 | 1.1 |
| Crospovidone | 2 | 6 | 2 | 4.4 |
| Total | 100 | 300 | 100 | 220 |

#equivalent to 50 mg of 1-[(2-bromophenyl)sulfonyl]-5-methoxy-3-[(4-methyl-1-piperazinyl) methyl]-1H-indole (free ase compound)

| | Example 32 | | Example 33 | |
|---|---|---|---|---|
| Ingredient | (% w/w) | mg/tablet | (% w/w) | mg/tablet |
| Compound 1 | 12.35 | 74.1# | 49.67 | 74.51# |
| Microcrystalline cellulose (Avicel PH 102) | 84.15 | 504.9 | 49.83 | 70.24 |
| Magnesium stearate | 1 | 6 | 1 | 1.5 |
| Colloidal silicon dioxide (Aerosil ®) | 0.5 | 3 | 0.5 | 0.75 |
| Crospovidone | 2 | 12 | 2 | 3 |
| Total | 100 | 600 | 100 | 150 |

#equivalent to 50 mg of 1-[(2-bromophenyl)sulfonyl]-5-methoxy-3-[(4-methyl-1-piperazinyl) methyl]-1H-indole (free base compound)

Example 34 to 37

Composition of 75 mg Dose IR Tablets:

| | Example 34 | | Example 35 | |
|---|---|---|---|---|
| Ingredient | (% w/w) | mg/tablet | (% w/w) | mg/tablet |
| Compound 1 | 37.25 | 111.75# | 50.79 | 111.74# |
| Microcrystalline cellulose (Avicel PH 102) | 59.25 | 177.75 | 45.71 | 100.56 |
| Magnesium stearate | 1 | 3 | 1 | 2.2 |
| Colloidal silicon dioxide (Aerosil ®) | 0.5 | 1.5 | 0.5 | 1.1 |
| Crospovidone | 2 | 6 | 2 | 4.4 |
| Total | 100 | 300 | 100 | 220 |

#equivalent to 75 mg of 1-[(2-bromophenyl)sulfonyl]-5-methoxy-3-[(4-methyl-1-piperazinyl) methyl]-1H-indole (free base compound)

| | Example 36 | | Example 37 | |
|---|---|---|---|---|
| Ingredient | (% w/w) | mg/tablet | (% w/w) | mg/tablet |
| Compound 1 | 50.8 | 111.76# | 50.8 | 111.76# |
| Microcrystalline cellulose (Avicel PH 102) | 47.7 | 104.94 | — | — |
| Starch (Starlac) | — | — | 47.7 | 104.98 |
| Magnesium stearate | 1 | 2.2 | 1 | 2.2 |
| Colloidal silicon dioxide (Aerosil ®) | 0.5 | 1.1 | 0.5 | 1.1 |
| Total | 100 | 220 | 100 | 220 |

#equivalent to 75 mg of 1-[(2-bromophenyl)sulfonyl]-5-methoxy-3-[(4-methyl-1-piperazinyl) methyl]-1H-indole (free base compound)

Examples 38 to 44

Composition of 100 mg Dose IR Tablets:

| | Example 38 | | Example 39 | |
|---|---|---|---|---|
| Ingredient | (% w/w) | mg/tablet | (% w/w) | mg/tablet |
| Compound 1 | 49.36 | 148.08# | 49.37 | 148.11# |
| Microcrystalline cellulose (Avicel PH 102) | 49.14 | 147.42 | 49.13 | 147.39 |

-continued

| Ingredient | Example 38 (% w/w) | Example 38 mg/tablet | Example 39 (% w/w) | Example 39 mg/tablet |
|---|---|---|---|---|
| Magnesium stearate | 1 | 3 | 1 | 3 |
| Colloidal silicon dioxide (Aerosil ®) | 0.5 | 1.5 | 0.5 | 1.5 |
| Total | 100 | 300 | 100 | 300 |

#equivalent to 100 mg of 1-[(2-bromophenyl)sulfonyl]-5-methoxy-3-[(4-methyl-1-piperazinyl) methyl]-1H-indole (free base compound)

| Ingredient | Example 40 (% w/w) | Example 40 mg/tablet | Example 41 (% w/w) | Example 41 mg/tablet |
|---|---|---|---|---|
| Compound 1 | 59.24 | 148.1# | 37.03 | 148.12# |
| Microcrystalline cellulose (Avicel PH 102) | 39.26 | 98.15 | 61.47 | 245.88 |
| Magnesium stearate | 1 | 2.5 | 1 | 4 |
| Colloidal silicon dioxide (Aerosil ®) | 0.5 | 1.25 | 0.5 | 2 |
| Total | 100 | 250 | 100 | 400 |

#equivalent to 100 mg of 1-[(2-bromophenyl)sulfonyl]-5-methoxy-3-[(4-methyl-1-piperazinyl) methyl]-1H-indole (free base compound)

| Ingredient | Example 42 (% w/w) | Example 42 mg/tablet | Example 43 (% w/w) | Example 43 mg/tablet |
|---|---|---|---|---|
| Compound 1 | 49.67 | 149.01# | 59.6 | 149# |
| Microcrystalline cellulose (Avicel PH 102) | 47.33 | 141.99 | 36.9 | 92.25 |
| Magnesium stearate | 0.5 | 1.5 | 1 | 2.5 |
| Colloidal silicon dioxide (Aerosil ®) | 0.5 | 1.5 | 0.5 | 1.25 |
| Crospovidone | 2 | 6 | 2 | 5 |
| Total | 100 | 300 | 100 | 250 |

#equivalent to 100 mg of 1-[(2-bromophenyl)sulfonyl]-5-methoxy-3-[(4-methyl-1-piperazinyl) methyl]-1H-indole (free base compound)

| Ingredient | Example 44 (% w/w) | Example 44 mg/tablet |
|---|---|---|
| Compound 1 | 24.7 | 148.2# |
| Microcrystalline cellulose (Avicel PH 102) | 71.8 | 430.8 |
| Magnesium stearate | 1 | 6 |
| Colloidal silicon dioxide (Aerosil ®) | 0.5 | 3 |
| Crospovidone | 2 | 12 |
| Total | 100 | 600 |

#equivalent to 100 mg of 1-[(2-bromophenyl)sulfonyl]-5-methoxy-3-[(4-methyl-1-piperazinyl) methyl]-1H-indole (free base compound)

Examples 45 to 46

Composition of 150 mg and 200 mg Dose IR Tablets:

| Ingredient | Example 45 (% w/w) | Example 45 mg/tablet | Example 46 (% w/w) | Example 46 mg/tablet |
|---|---|---|---|---|
| Compound 1 | 49.67 | 223.52* | 49.67 | 298.02# |
| Microcrystalline cellulose (Avicel PH 102) | 46.83 | 210.73 | 46.83 | 280.98 |
| Magnesium stearate | 1 | 4.5 | 1 | 6 |
| Colloidal silicon dioxide (Aerosil ®) | 0.5 | 2.25 | 0.5 | 3 |
| Crospovidone | 2 | 9 | 2 | 12 |
| Total | 100 | 450 | 100 | 600 |

*equivalent to 150 mg of 1-[(2-bromophenyl)sulfonyl]-5-methoxy-3-[(4-methyl-1-piperazinyl) methyl]-1H-indole (free base compound)

#equivalent to 200 mg of 1-[(2-bromophenyl)sulfonyl]-5-methoxy-3-[(4-methyl-1-piperazinyl) methyl]-1H-indole (free base compound)

Example 47

Preparation of IR Tablet Using Wet Granulation Method Composition of 50 mg IR Tablet:

| Ingredient | % w/w | mg/tablet |
|---|---|---|
| Compound 1 | 24.67 | 74# |
| Microcrystalline cellulose (Avicel PH 102) | 66.83 | 200.5 |
| Povidone | 4.0 | 12 |
| Crospovidone | 3.0 | 9 |
| Magnesium stearate | 1.0 | 3 |
| Colloidal silicon dioxide (Aerosil ®) | 0.5 | 1.5 |
| Total | 100 | 300 |

#equivalent to 50 mg of 1-[(2-bromophenyl)sulfonyl]-5-methoxy-3-[(4-methyl-1-piperazinyl) methyl]-1H-indole (free base compound)

Method of Preparing IR Tablet:

All the ingredients were accurately weighed (Compound 1 of 24.67%, Avicel PH 102 of 66.83% and crospovidone of 3%) and sieved using sieve number 40. The sieved compound 1, Avicel PH 102 and crospovidone were blended for 10 minutes in an octagonal blender. The mixture obtained was transferred into RMG and added povidone binder solution (povidone (4%) was dissolved in purified water) dropwise to RMG to form cohesive mass. The blend obtained was dried in a tray drier at 50° C. Dried blend was passed through #18 mesh to form granules. The granules obtained were mixed with magnesium stearate and aerosil and the mixture was blended for 10 minutes in an octagonal blender. The lubricated blend was compressed using 9 mm round concave punches and dies on rotary compression machine to obtain 300 mg tablet.

Examples 48 to 49

The following examples are prepared by following the method of preparation of example 47.

Composition of 50 mg IR Tablets:

| | Example 48 | | Example 49 | |
|---|---|---|---|---|
| Ingredient | (% w/w) | mg/tablet | (% w/w) | mg/tablet |
| Compound 1 | 24.67 | 74# | 24.67 | 74# |
| Microcrystalline cellulose (Avicel PH 102) | 65.83 | 197.5 | 64.83 | 194.5 |
| Povidone (PVP K30) | 4.0 | 12 | — | — |
| HPMC | — | — | 5.0 | 15 |
| Sodium starch glycolate | 4.0 | 12 | — | — |
| Croscarmellose sodium | — | — | 4.0 | 12 |
| Magnesium stearate | 1 | 3 | 1 | 3 |
| Aerosil | 0.5 | 1.5 | 0.5 | 1.5 |
| Total | 100 | 300 | 100 | 300 |

#equivalent to 50 mg of 1-[(2-bromophenyl)sulfonyl]-5-methoxy-3-[(4-methyl-1-piperazinyl) methyl]-1H-indole (free Base compound)

Example 50 to 51

The examples 50 to 51 were prepared by following the method of preparation of example 2 by using appropriate amount of active ingredient, diluent, disintegrant, lubricant, and glidant.

Composition of 50 mg and 100 mg IR Tablets:

| | Example 50 | |
|---|---|---|
| Ingredients | (% w/w) | mg/tablet |
| Compound 1 | 24 | 72# |
| Microcrystalline cellulose (Avicel PH 102) | 74 | 222 |
| Magnesium stearate | 1 | 3 |
| Colloidal silicon dioxide (Aerosil ®) | 0.5 | 1.5 |
| Crospovidone | 0.5 | 1.5 |
| Total | 100 | 300 |

#equivalent to 50 mg of 1-[(2-bromophenyl)sulfonyl]-5-methoxy-3-[(4-methyl-1-piperazinyl) methyl]-1H-indole (free base compound)

| | Example 51 | |
|---|---|---|
| Ingredients | (% w/w) | mg/tablet |
| Compound 1 | 48 | 144# |
| Microcrystalline cellulose (Avicel PH 102) | 48.5 | 145.5 |
| Magnesium stearate | 1 | 3 |
| Colloidal silicon dioxide (Aerosil ®) | 0.5 | 1.5 |
| Crospovidone | 2 | 6 |
| Total | 100 | 300 |

#equivalent to 100 mg of 1-[(2-bromophenyl)sulfonyl]-5-methoxy-3-[(4-methyl-1-piperazinyl) methyl]-1H-indole (free base compound)

Example 52

Dissolution Studies of IR Tablets

The dissolution studies were conducted for the immediate release tablets of the instant invention to demonstrate the % release of active ingredient at different time intervals.

Protocol:

Dissolution was carried out in accordance with the United States pharmacopeia general procedures using dissolution apparatus II (paddle method). The IR tablet was placed in 900 mL of simulated gastric fluid (pH 1.2), 0.1N hydrochloric acid or water at 37° C. with a paddle speed of 50 rpm/100 rpm and measuring the amount of active ingredient dissolved (especially, using UV at 255 nm or using HPLC, wavelength 220 nm) at 15 and 30 minutes.

Results:

The dissolution studies data of the IR tablets are tabulated below.

| S. No | Examples | Time (minutes) | % of Active ingredient release |
|---|---|---|---|
| 1 | Example 2 | 15 | 97 |
| | | 30 | 97 |
| 2 | Example 3 | 15 | 108 |
| | | 30 | 105 |
| 3 | Example 4 | 15 | 85 |
| | | 30 | 97 |
| 4 | Example 6 | 15 | 103 |
| | | 30 | 106 |
| 5 | Example 7 | 15 | 103 |
| | | 30 | 103 |
| 6 | Example 10 | 15 | 100 |
| | | 30 | 100 |
| 7 | Example 11 | 15 | 102 |
| | | 30 | 102 |
| 8 | Example 12 | 15 | 102 |
| | | 30 | 101 |
| 9 | Example 13 | 15 | 98 |
| | | 30 | 98 |
| 10 | Example 14 | 15 | 100 |
| | | 30 | 99 |
| 11 | Example 15 | 15 | 102 |
| | | 30 | 107 |
| 12 | Example 15 | 15 | 107 |
| | | 30 | 106 |
| 13 | Example 17 | 15 | 101 |
| | | 30 | 103 |
| 14 | Example 18 | 15 | 99 |
| | | 30 | 99 |
| 15 | Example 20 | 15 | 98 |
| | | 30 | 97 |
| 16 | Example 21 | 15 | 104 |
| | | 30 | 103 |
| 17 | Example 22 | 15 | 102 |
| | | 30 | 106 |
| 18 | Example 25 | 15 | 104 |
| | | 30 | 104 |
| 19 | Example 27 | 15 | 98 |
| | | 30 | 100 |
| 20 | Example 28 | 15 | 102 |
| | | 30 | 101 |
| 21 | Example 32 | 15 | 98 |
| | | 30 | 96 |
| 22 | Example 33 | 15 | 98 |
| | | 30 | 102 |
| 23 | Example 35 | 15 | 101 |
| | | 30 | 101 |
| 24 | Example 36 | 15 | 100 |
| | | 30 | 100 |
| 25 | Example 37 | 15 | 106 |
| | | 30 | 108 |
| 26 | Example 41 | 15 | 82 |
| | | 30 | 94 |
| 27 | Example 42 | 15 | 105 |
| | | 30 | 105 |

-continued

| S. No | Examples | Time (minutes) | % of Active ingredient release |
|---|---|---|---|
| 28 | Example 44 | 15 | 101 |
| | | 30 | 99 |
| 29 | Example 45 | 15 | 98 |
| | | 30 | 96 |
| 30 | Example 46 | 15 | 99 |
| | | 30 | 99 |
| 31 | Example 47 | 15 | 99 |
| | | 30 | 99 |
| 32 | Example 48 | 15 | 100 |
| | | 30 | 100 |
| 33 | Example 49 | 15 | 101 |
| | | 30 | 101 |

Example 53

Stability Study of IR Tablets

The stability study was conducted to assess the stability of the immediate release tablets and the impurity profile of the instant invention under different storage conditions.

The stability studies were carried out at ambient temperature (25±2° C./65±5% RH), accelerated storage (40±2° C./75±5% RH), and 60° C. oven for 6 months.

Protocol:

The immediate release tablets are packed in HDPE bottles with polyethylene liners with desiccant for a period of 6 months at different storage conditions. The samples were analyzed for purity using HPLC.

Results:

Dissolution:

The dissolution data of examples for different time points at accelerated storage conditions are tabulated below.

| | | | % of Active ingredient release | | | |
|---|---|---|---|---|---|---|
| S. No | Examples | Time (minutes) | Day 1 | 1 month | 3 months | 6 months |
| 1 | Example 13 | 30 | 106 | 106 | 90 | 104 |
| 2 | Example 15 | 30 | 91 | 99 | 89 | 97 |

-continued

| | | | % of Active ingredient release | | | |
|---|---|---|---|---|---|---|
| S. No | Examples | Time (minutes) | Day 1 | 1 month | 3 months | 6 months |
| 3 | Example 16 | 30 | 98 | 99 | 103 | 102 |
| 4 | Example 17 | 30 | 99 | 100 | 103 | 99 |
| 5 | Example 32 | 30 | 96 | 99 | 100 | 102 |
| 6 | Example 33 | 30 | 102 | 101 | 100 | 99 |
| 7 | Example 44 | 30 | 99 | 99 | 99 | 99 |
| 8 | Example 50 | 30 | 102 | 101 | 99 | 100 |
| 9 | Example 51 | 30 | 101 | 100 | 100 | 102 |

The dissolution data of examples 50 and 51 for different time points at ambient storage conditions are tabulated below.

| | % of Active ingredient release (in 30 minutes) | |
|---|---|---|
| Storage time | Example 50 | Example 51 |
| Initial | 102 | 101 |
| 1 month | 100 | 99 |
| 3 months | 100 | 100 |
| 6 months | 103 | 101 |
| 9 months | 102 | 103 |
| 12 months | 102 | 102 |
| 18 months | 100 | 100 |
| 24 months | 102 | 97 |
| 36 months | 100 | 101 |
| 44 months | 101 | 101 |
| 48 months | 102 | 101 |
| 60 months | 101 | 103 |

Conclusion:

We observed no significant variation in dissolution of the IR tablets after storing for 6 months at accelerated storage conditions (i.e, temperature 40±2° C. at 75±5% relative humidity (RH)).

Further no significant variation was observed in dissolution of the IR tablets after storing for 60 months at ambient storage conditions.

Purity:

The purity of IR tablet on day 1 is tabulated below.

| S. No | Example number | Dose (mg) | Purity of active ingredient (%) | Chloro impurity (%) | Maximum unknown impurity (%) | Other unknown impurities (%) | Total impurities (%) |
|---|---|---|---|---|---|---|---|
| 1 | 13 | 75 | 99.64 | 0.19 | 0.06 | 0.11 | 0.36 |
| 2 | 15 | 75 | 99.66 | 0.19 | 0.06 | 0.09 | 0.34 |
| 3 | 17 | 75 | 99.64 | 0.20 | 0.06 | 0.10 | 0.36 |

The purity of IR tablets under different storage conditions at the end of 6 months is tabulated below.

| S. No | Example number | Dose (mg) | Storage conditions | Purity (%) | Chloro impurity (%) | Maximum unknown impurity (%) | Other impurities (%) | Total impurities (%) |
|---|---|---|---|---|---|---|---|---|
| 1 | 13 | 75 | 60° C. Oven | 99.38 | 0.21 | 0.09 | 0.32 | 0.62 |
| 2 | 13 | 75 | 40° C./ 75% RH | 99.63 | 0.19 | 0.06 | 0.12 | 0.37 |
| 3 | 15 | 75 | 40° C./ 75% RH | 99.64 | 0.19 | 0.06 | 0.11 | 0.36 |

-continued

| S. No | Example number | Dose (mg) | Storage conditions | Purity (%) | Chloro impurity (%) | Maximum unknown impurity (%) | Other impurities (%) | Total impurities (%) |
|---|---|---|---|---|---|---|---|---|
| 4 | 17 | 75 | 60° C. Oven | 99.37 | 0.20 | 0.08 | 0.35 | 0.63 |
| 5 | 17 | 75 | 40° C./ 75% RH | 99.62 | 0.20 | 0.06 | 0.12 | 0.38 |

The purity of IR tablets under accelerated conditions (40° C./75% RH) for 6 months is tabulated below.

| Examples | Test | Initial | 1 month | 2 months | 3 months | 6 months |
|---|---|---|---|---|---|---|
| Example 50 | Chloro impurity (%) | 0.19 | 0.18 | 0.19 | 0.19 | 0.17 |
| | Maximum Unknown impurity (%) | 0.03 | 0.03 | 0.03 | 0.02 | 0.03 |
| | Total impurities (%) | 0.22 | 0.21 | 0.22 | 0.21 | 0.2 |
| Example 51 | Chloro impurity (%) | 0.19 | 0.19 | 0.19 | 0.19 | 0.17 |
| | Maximum Unknown impurity (%) | 0.03 | 0.03 | 0.02 | 0.03 | 0.03 |
| | Total impurities (%) | 0.22 | 0.22 | 0.21 | 0.22 | 0.2 |

The purity of IR tablets under ambient conditions for 60 months is tabulated below.

| | Examples | | | | | |
|---|---|---|---|---|---|---|
| | Example 50 | | | Example 51 | | |
| Test | Chloro impurity (%) | Maximum Unknown impurity (%) | Total impurities (%) | Chloro impurity (%) | Maximum Unknown impurity (%) | Total impurities (%) |
| Initial | 0.19 | 0.03 | 0.22 | 0.19 | 0.02 | 0.21 |
| 1 month | 0.18 | 0.02 | 0.2 | 0.19 | 0.03 | 0.22 |
| 3 months | 0.19 | 0.03 | 0.22 | 0.19 | 0.03 | 0.22 |
| 6 months | 0.17 | 0.03 | 0.2 | 0.17 | 0.03 | 0.2 |
| 9 months | 0.16 | 0.03 | 0.21 | 0.16 | 0.03 | 0.21 |
| 12 months | 0.21 | 0.04 | 0.28 | 0.22 | 0.04 | 0.29 |
| 18 months | 0.21 | 0.03 | 0.24 | 0.21 | 0.03 | 0.26 |
| 24 months | 0.19 | 0.03 | 0.24 | 0.19 | 0.03 | 0.26 |
| 36 months | 0.2 | 0.04 | 0.27 | 0.2 | 0.04 | 0.28 |
| 44 months | 0.21 | 0.04 | 0.28 | 0.21 | 0.04 | 0.29 |
| 48 months | 0.21 | 0.04 | 0.27 | 0.21 | 0.04 | 0.29 |
| 60 months | 0.19 | 0.05 | 0.27 | 0.2 | 0.04 | 0.28 |

Conclusion:

We observed no significant variation in purity of the active ingredient under different storage conditions. As evident from the above stability data the active ingredient in immediate release tablets of instant invention is stable at least six months under accelerated storage condition.

It was also observed that the active ingredient in immediate release tablets of the instant invention is stable for at least 60 months under ambient storage condition.

Example 54

In-Vivo Pharmacokinetic Study of IR Tablets

The dog pharmacokinetic study is conducted to confirm the dissolution data of Compound 1.

Experimental Procedure of Dog Pharmacokinetic Study

Male beagle dogs (10±2 kg) were used as experimental animals. Each dog was housed in individual cages. Animals were fasted over night before oral dosing (p.o) and food pellets were allowed 2 hours post dosing. Two beagle dogs (~11 mg/kg) were dosed orally with IR tablets prepared by pharmaceutical compositions disclosed in Example 42.

At each time point, blood (0.5 mL) was collected through cephalic vein. Collected blood was transferred into a labeled eppendroff tube containing 10 μL of heparin as anticoagulant. Typically blood samples were collected at following time points: Pre dose, 0.25, 0.5, 1, 1.5, 2, 3, 5, 7, 12, 24, 30 and 48 hours post dose (n=2). Blood was centrifuged at 4000 rpm for 10 minutes. Plasma was separated and stored at −20° C. until analysis. The concentrations of active ingredient were quantified in plasma by validated LC-MS/MS method using suitable extraction technique. The active ingredient was quantified in the calibration range around 0.2-200 ng/mL.

Pharmacokinetic parameters $C_{max}$, $T_{max}$, $AUC_{0-t}$ and $T_{1/2}$ were calculated by using standard non-compartmental model Phoenix WinNonlin 6.2 version Software package.

The results of this study are tabulated below.

| Strain/ Gender | Dose (mg/kg) | Dosage form | $C_{max}$ (ng/mL) | $T_{max}$ (hours) | $AUC_{0-t}$ (ng · hour/mL) | $T_{1/2}$ (hours) |
|---|---|---|---|---|---|---|
| Beagle dog | ~11 | Tablet | 60 ± 16 | 1.25 ± 0.35 | 251 ± 27 | 5.97 ± 0.40 |

The invention claimed is:

1. An immediate release pharmaceutical composition on a total of 100% by weight comprising, (a) from about 2% to about 60% 1-[(2-bromophenyl) sulfonyl]-5-methoxy-3-[(4-methyl-1-piperazinyl) methyl]-1H-indole or a pharmaceutically acceptable salt thereof;

(b) from about 36% to about 97% diluent; wherein said diluent is selected from microcrystalline cellulose, lactose monohydrate, dibasic calcium phosphate, lactose, lactose hydrate, lactose anhydrate, mannitol, starch or isomalt;

(c) from about 0.5% to about 2% lubricant; wherein the lubricant is magnesium stearate; and (d) from about 0.5% to about 1% glidant: wherein the glidant is colloidal silicon dioxide;

wherein the immediate release pharmaceutical composition provides an in-vitro release of not less than about 95 wt % of 1-[(2-bromophenyl) sulfonyl]-5-methoxy-3-[(4-methyl-1-piperazinyl) methyl]-1H-indole or a pharmaceutically acceptable salt thereof within about 30 minutes of dissolution in not less than about 900 mL of: a fluid with a pH of about 1.2, 0.1N hydrochloric acid, or water; and wherein after storage for at least 60 months under ambient storage conditions, the composition has not more than 0.5% of chloro impurities; not more than 0.5% unknown impurities; and not more than 1% total impurities.

2. The immediate release pharmaceutical composition as claimed in claim 1, wherein the composition on a total of 100% by weight comprising, (a) from about 2% to about 60% 1-[(2-bromophenyl) sulfonyl]-5-methoxy-3-[(4-methyl-1-piperazinyl) methyl]-1H-indole dimesylate monohydrate;

(b) from about 36% to about 97% diluent; wherein said diluent is selected from microcrystalline cellulose, lactose monohydrate, dibasic calcium phosphate, lactose, lactose hydrate, lactose anhydrate, mannitol, starch or isomalt;

(c) from about 0.5% to about 2% lubricant; wherein the lubricant is magnesium stearate; and (d) from about 0.5% to about 1% glidant; wherein the glidant is colloidal silicon dioxide;

wherein the immediate release pharmaceutical composition provides an in-vitro release of not less than about 95 wt % of 1-[(2-bromophenyl) sulfonyl]-5-methoxy-3-[(4-methyl-1-piperazinyl) methyl]-1H-indole or a pharmaceutically acceptable salt thereof within about 30 minutes of dissolution in not less than about 900 mL of: a fluid with a pH of about 1.2, 0.1N hydrochloric acid, or water; and wherein after storage for at least 60 months under ambient storage conditions, the composition has not more than 0.5% of chloro impurities; not more than 0.5% unknown impurities; and not more than 1% total impurities.

3. The immediate release pharmaceutical composition as claimed in claim 2, wherein the composition on a total of 100% by weight comprising, (a) from about 2% to about 60% 1-[(2-bromophenyl) sulfonyl]-5-methoxy-3-[(4-methyl-1-piperazinyl) methyl]-1H-indole or a pharmaceutically acceptable salt thereof;

(b) from about 36% to about 97% diluent; wherein said diluent is selected from microcrystalline cellulose, lactose monohydrate, dibasic calcium phosphate, lactose, lactose hydrate, lactose anhydrate, mannitol, starch or isomalt;

(c) from about 0.5% to about 2% lubricant; wherein the lubricant is magnesium stearate;

(d) from about 0.5% to about 1% glidant; wherein the glidant is colloidal silicon dioxide; and (e) from about 0.5% to about 5% disintegrant; wherein the disintegrant is selected from crospovidone, sodium starch glycolate or croscarmellose sodium;

wherein the immediate release pharmaceutical composition provides an in-vitro release of not less than about 95 wt % of 1-[(2-bromophenyl) sulfonyl]-5-methoxy-3-[(4-methyl-1-piperazinyl) methyl]-1H-indole or a pharmaceutically acceptable salt thereof within about 30 minutes of dissolution in not less than about 900 mL of: a fluid with a pH of about 1.2, 0.1N hydrochloric acid, or water; and wherein after storage for at least 60 months under ambient storage conditions, the composition has not more than 0.5% of chloro impurities; not more than 0.5% unknown impurities; and not more than 1% total impurities.

4. The immediate release pharmaceutical composition as claimed in claim 2, wherein the composition on a total of 100% by weight comprising, (a) from about 2% to about 60% 1-[(2-bromophenyl) sulfonyl]-5-methoxy-3-[(4-methyl-1-piperazinyl) methyl]-1H-indole dimesylate monohydrate;

(b) from about 36% to about 97% diluent; wherein said diluent is selected from microcrystalline cellulose, lactose monohydrate, dibasic calcium phosphate, lactose, lactose hydrate, lactose anhydrate, mannitol, starch or isomalt;

(c) from about 0.5% to about 2% lubricant; wherein the lubricant is magnesium stearate;

(d) from about 0.5% to about 1% glidant; wherein the glidant is colloidal silicon dioxide; and (e) from about 0.5% to about 5% disintegrant; wherein the disintegrant is selected from crospovidone, sodium starch glycolate or croscarmellose sodium;

wherein the immediate release pharmaceutical composition provides an in-vitro release of not less than about 95 wt % of 1-[(2-bromophenyl) sulfonyl]-5-methoxy-3-[(4-methyl-1-piperazinyl) methyl]-1H-indole or a pharmaceutically acceptable salt thereof within about 30 minutes of dissolution in not less than about 900 mL of: a fluid with a pH of about 1.2, 0.1N hydrochloric acid, or water; and wherein after storage for at least 60 months under ambient storage conditions, the composition has not more than 0.5% of chloro impurities; not more than 0.5% unknown impurities; and not more than 1% total impurities.

5. The immediate release pharmaceutical composition as claimed in claim 1, wherein the composition is in the form of tablet or capsule.

6. The immediate release pharmaceutical composition as claimed in claim 3, wherein the composition is in the form of tablet or capsule.

7. The immediate release pharmaceutical composition as claimed in claim 1, wherein the dosage of 1-[(2-bromophenyl) sulfonyl]-5-methoxy-3-[(4-methyl-1-piperazinyl) methyl]-1H-indole or a pharmaceutically acceptable salt thereof is about 5 mg to about 200 mg.

8. The immediate release pharmaceutical composition as claimed in claim 3, wherein the dosage of 1-[(2-bromophenyl) sulfonyl]-5-methoxy-3-[(4-methyl-1-piperazinyl) methyl]-1H-indole or a pharmaceutically acceptable salt thereof is about 5 mg to about 200 mg.

9. The immediate release pharmaceutical composition as claimed in claim 5, wherein the tablet on a total of 100% by weight comprising, (a) from about 2% to about 60% 1-[(2-bromophenyl) sulfonyl]-5-methoxy-3-[(4-methyl-1-piperazinyl) methyl]-1H-indole dimesylate monohydrate;

(b) from about 36% to about 97% microcrystalline cellulose;

(c) from about 0.5% to about 2% magnesium stearate; and (d) from about 0.5% to about 1% colloidal silicon dioxide.

10. The immediate release pharmaceutical composition as claimed in claim 6, wherein the tablet on a total of 100% by weight comprising, (a) from about 2% to about 60% 1-[(2-bromophenyl) sulfonyl]-5-methoxy-3-[(4-methyl-1-piperazinyl) methyl]-1H-indole dimesylate monohydrate;

(b) from about 36% to about 97% microcrystalline cellulose;

(c) from about 0.5% to about 2% magnesium stearate;

(d) from about 0.5% to about 1% colloidal silicon dioxide; and (e) from about 0.5% to about 4% crospovidone.

11. The immediate release pharmaceutical composition as claimed in claim 9, wherein the dosage of 1-[(2-bromophenyl) sulfonyl]-5-methoxy-3-[(4-methyl-1-piperazinyl) methyl]-1H-indole dimesylate monohydrate is about 5 mg to about 200 mg.

12. The immediate release pharmaceutical composition as claimed in claim 9, wherein the total weight of immediate release tablet is from about 100 mg to 600 mg.

13. The immediate release pharmaceutical composition as claimed in claim 10, wherein the dosage of 1-[(2-bromophenyl) sulfonyl]-5-methoxy-3-[(4-methyl-1-piperazinyl) methyl]-1H-indole dimesylate monohydrate is about 5 mg to about 200 mg.

14. The immediate release pharmaceutical composition as claimed in claim 10, wherein the total weight of immediate release tablet is from about 100 mg to 600 mg.

* * * * *